US009888883B2

United States Patent
Ellingsen et al.

(10) Patent No.: US 9,888,883 B2
(45) Date of Patent: Feb. 13, 2018

(54) SENSOR DEVICE FOR SENSING BODY FLUID DENSITY AND/OR MEMBRANE RESISTANCE

(75) Inventors: Olav Ellingsen, Oslo (NO); Bjarte Sorebo Ellingsen, Oslo (NO)

(73) Assignee: MECSENSE AS, Oslo (NO)

( * ) Notice: Subject to any disclaimer, the term of this patent is extended or adjusted under 35 U.S.C. 154(b) by 1124 days.

(21) Appl. No.: 13/979,348

(22) PCT Filed: Jan. 12, 2012

(86) PCT No.: PCT/NO2012/000003
§ 371 (c)(1),
(2), (4) Date: Sep. 4, 2013

(87) PCT Pub. No.: WO2012/096582
PCT Pub. Date: Jul. 19, 2012

(65) Prior Publication Data
US 2013/0338456 A1 Dec. 19, 2013

(30) Foreign Application Priority Data
Jan. 12, 2011 (NO) .................................. 20110070

(51) Int. Cl.
| A61B 5/00 | (2006.01) |
| A61B 5/145 | (2006.01) |
| G01N 9/24 | (2006.01) |
| G01N 9/26 | (2006.01) |
| A61B 5/01 | (2006.01) |
| A61B 5/11 | (2006.01) |
| A61B 5/1455 | (2006.01) |
| A61B 7/00 | (2006.01) |

(52) U.S. Cl.
CPC .......... *A61B 5/7278* (2013.01); *A61B 5/0051* (2013.01); *A61B 5/01* (2013.01); *A61B 5/11* (2013.01); *A61B 5/1455* (2013.01); *A61B 5/14532* (2013.01); *A61B 5/442* (2013.01); *A61B 5/443* (2013.01); *A61B 5/7225* (2013.01); *A61B 7/00* (2013.01); *G01N 9/24* (2013.01); *G01N 9/26* (2013.01); *A61B 5/6816* (2013.01)

(58) Field of Classification Search
CPC . A61B 5/14532; A61B 5/0048; A61B 5/0051; A61B 5/7278
See application file for complete search history.

(56) References Cited

U.S. PATENT DOCUMENTS

| 4,947,851 A | 8/1990 | Sarvazyan et al. |
| 5,115,808 A | 5/1992 | Popovic et al. |
| 5,119,819 A * | 6/1992 | Thomas ............. A61B 5/14532 |
| | | 600/347 |
| 5,606,971 A | 3/1997 | Sarvazyan |

(Continued)

FOREIGN PATENT DOCUMENTS

| JP | 2007-532172 A | 11/2007 |
| JP | 2009-533180 A | 9/2009 |

(Continued)

*Primary Examiner* — Christian Jang
(74) *Attorney, Agent, or Firm* — Knobbe, Martens, Olson & Bear, LLP

(57) ABSTRACT

The present invention relates to a sensor device for measuring tensile variation against a membrane separating a liquid such as the skin on humans and animals and any other membrane separating a liquid on one of its sides.

7 Claims, 12 Drawing Sheets

(56) References Cited

U.S. PATENT DOCUMENTS

| | | | |
|---|---|---|---|
| 5,810,731 A | 9/1998 | Sarvazyan et al. | |
| 6,150,941 A * | 11/2000 | Geiger | A61B 5/113 340/573.1 |
| 6,405,069 B1 | 6/2002 | Oraevsky et al. | |
| 7,608,043 B1 | 10/2009 | Lee et al. | |
| 2001/0053384 A1* | 12/2001 | Greenleaf | A61K 41/0047 424/450 |
| 2003/0065263 A1* | 4/2003 | Hare | A61B 17/22012 600/439 |
| 2004/0065143 A1 | 4/2004 | Husher | |
| 2004/0199058 A1* | 10/2004 | Karam | A61B 5/14539 600/306 |
| 2004/0225215 A1 | 11/2004 | Querleux et al. | |
| 2005/0015001 A1 | 1/2005 | Lec et al. | |
| 2005/0043602 A1 | 2/2005 | Freger et al. | |
| 2005/0148899 A1 | 7/2005 | Walker et al. | |
| 2008/0154107 A1* | 6/2008 | Jina | A61B 5/14514 600/347 |
| 2009/0093977 A1 | 4/2009 | Hauptmann et al. | |
| 2009/0270695 A1* | 10/2009 | McEowen | A61B 5/02007 600/301 |
| 2011/0263956 A1 | 10/2011 | Gal et al. | |

FOREIGN PATENT DOCUMENTS

| | | |
|---|---|---|
| JP | 2010-526646 A | 8/2010 |
| WO | WO 2005/096936 A1 | 10/2005 |
| WO | WO 2007/121209 A2 | 10/2007 |
| WO | WO 2008/141306 A2 | 11/2008 |
| WO | WO 2009/139522 A1 | 11/2009 |
| WO | WO 2010/128500 A2 | 11/2010 |

* cited by examiner

Fig. 5
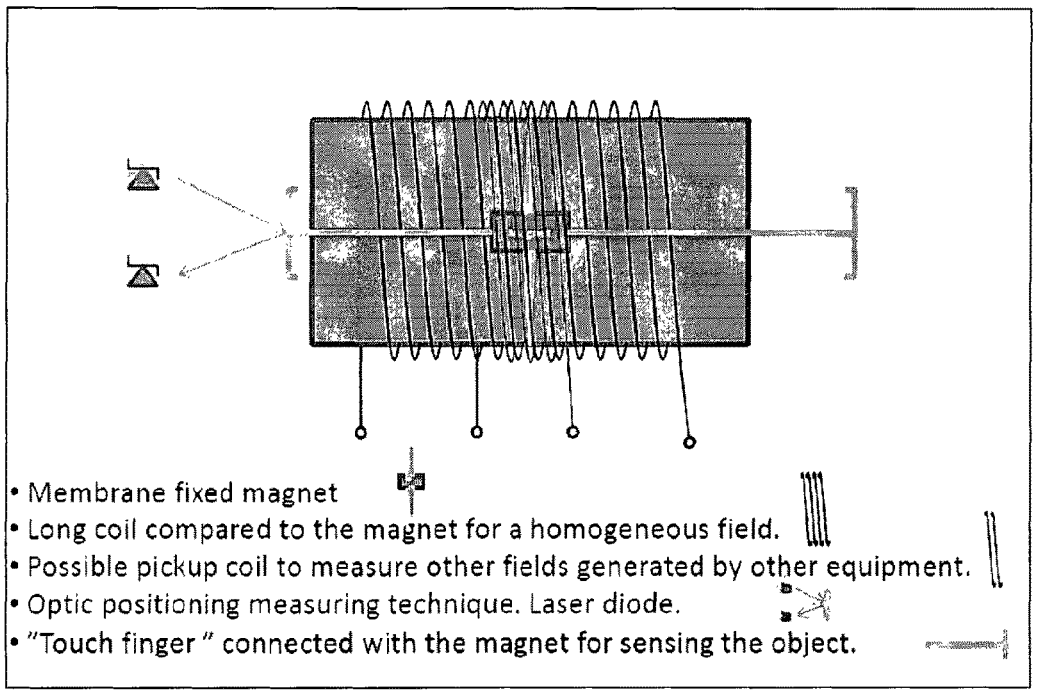
- Membrane fixed magnet
- Long coil compared to the magnet for a homogeneous field.
- Possible pickup coil to measure other fields generated by other equipment.
- Optic positioning measuring technique. Laser diode.
- "Touch finger" connected with the magnet for sensing the object.
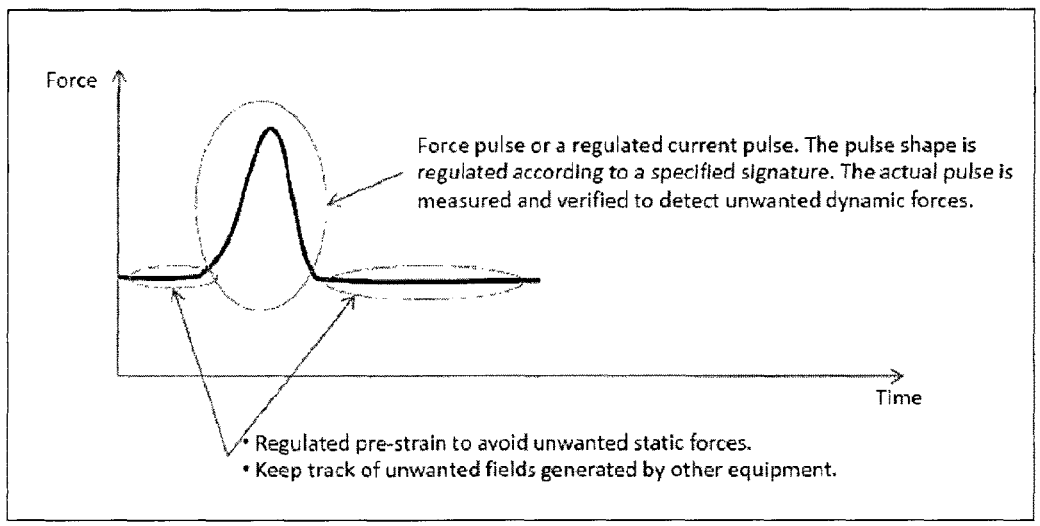
Fig. 6

SENSOR DEVICE FOR SENSING BODY FLUID DENSITY AND/OR MEMBRANE RESISTANCE

FIELD OF THE INVENTION

The present invention is related to a sensor for measuring tensile variation against a membrane separating a liquid such as the skin on humans and animals and any other membrane separating a liquid on one of its sides.

BACKGROUND OF THE INVENTION

The tensile stress or resistance of a membrane is dependent upon a number of factors, such as the elasticity of the membrane and the density of the liquid separated by the membrane.

A special case of interest is the tensile variation of the skin which can be interpreted as caused by the variation of the density of the body fluid. One such substance which causes rapid variation of the composition of the body fluids is its content of glucose. As the variations of glucose in diabetics are of paramount importance for the patients, measuring the glucose level in diabetics has been recognized for decades. Some 30 years ago, the only way to measure the glucose level was to apply a drop of blood on a strip where the color on the strip changed by the glucose level. The color was compared on a bar showing the corresponding glucose level for each color. As this principle was inaccurate, the industry started to develop electronic devices which electrically could detect the glucose level on a strip with a blood sample. Over the years this technology has resulted in a number of different devices varying in size, design and features.

Even though these meters represent a vast benefit to diabetics, they are not continuous, and all need a blood sample. Thus extensive research has been carried out in order to develop a continuous glucose sensor without the need of a blood sample.

Today there exist invasive glucose sensors that are continuous. A needle has to be inserted through the skin whereby interstitial liquid can be drawn to the sensor which by the aid of glucose oxidase shows varying glucose levels on a handheld receiver. The drawback is that the technology is invasive, and that the needle from time to time has to be changed. Unfortunately the injection site may also become inflamed whereby the users have to stop using the device because of discomfort.

The dream has been and is to develop a sensor which is non-invasive or implanted. One such approach has been to use the absorption of a beam of infrared light through the skin. However, as the absorption of the spectra in water is far greater than that of glucose this approach is very difficult in order to get reliable glucose data.

SUMMARY OF THE INVENTION

The present invention provides a sensor for measuring the density of a body, or the resistance of a membrane such as human skin, in a non-invasive manner, comprising a pulse generator, a temperature sensor and a transducer for registration of the speed of the pulse as a function of the body fluid and the elasticity of the skin, wherein said transducer is connected to a microprocessor in which the signal from the transducer is transformed into values for the relative density of said body fluid.

In a preferred embodiment of the present invention the pulse generating device generates a pulse in the form of a mechanical pulse, a vibrating force, a compressed air/liquid pulse or a sound wave.

In one embodiment of the invention the pulse generated is a mechanical pulse, which may be generated by an electromagnet or a magneto-strictive material and where the detection of the pulse is recorded by a detection coil or by a variable capacitor, light diode, accelerometer, microphone or any other sensitive pick up device capable of monitoring the impact of the mechanical pulse.

In another embodiment of the invention the mechanical pulse can be a single pulse, a pulse train or in the form of vibrations.

In another embodiment of the invention the mechanical pulse can be generated by a pneumatic or hydraulic impulse.

In another embodiment of the invention the recorded values are computed to give the rate of the changes of the glucose values and where the rate is shown on a display either in digits and/or graphs with associated warnings and recommendations to the user.

BRIEF DESCRIPTION OF THE DRAWINGS

The following drawings show examples of the principle of the invention, but it is to be understood that any design can be applied to exploit the principle in detecting the variations of the density in body fluid as a measure for detecting variation of the concentration of a solute in the liquid, without deviating from the present invention, which is limited solely by the claims of this invention.

Below the invention will be described in more detail by reference to the enclosed drawing, wherein:

FIG. 5 shows the layout of the pulse generator in the embodiment illustrated in FIG. 4.

FIG. 6 shows the pulse shape generated by the pulse generator of FIG. 5.

DETAILED DESCRIPTION OF THE PREFERRED EMBODIMENT

The objective of this invention is not to measure the actual density of the body fluid. This could be done by extracting body fluid with a syringe for measurement in a laboratory with i.e. a density meter made by Mettler Toledo. We are measuring the relative and varying density of the body fluid through the skin. The density is dependent on the composition of the fluid in its bodily environment. Due to cell membranes in tissues and muscles the density or viscosity of the body fluid will be higher inside the body than outside when applying a mechanical pulse impact on the skin. All physical objects in the body like bones will as well impact the relative density we measure. Dependent on the location of the sensor it will need to be calibrated using a standard glucose sensor. The density measurement value is dependent on the location of the sensor due to bodily structures. Once it is calibrated it will detect variations from that set point.

In addition to show the glucose values, a continuous reading of the values would give an even more important value for the diabetics. By continuous monitoring of the development of the glucose values, it is possible to compute the rate by which the values fall and rise. By present readings which give an exact number, it is not possible to see how fast the values are changing. This is shown in FIG. 15 for readings over 24 hours.

Figure 15:
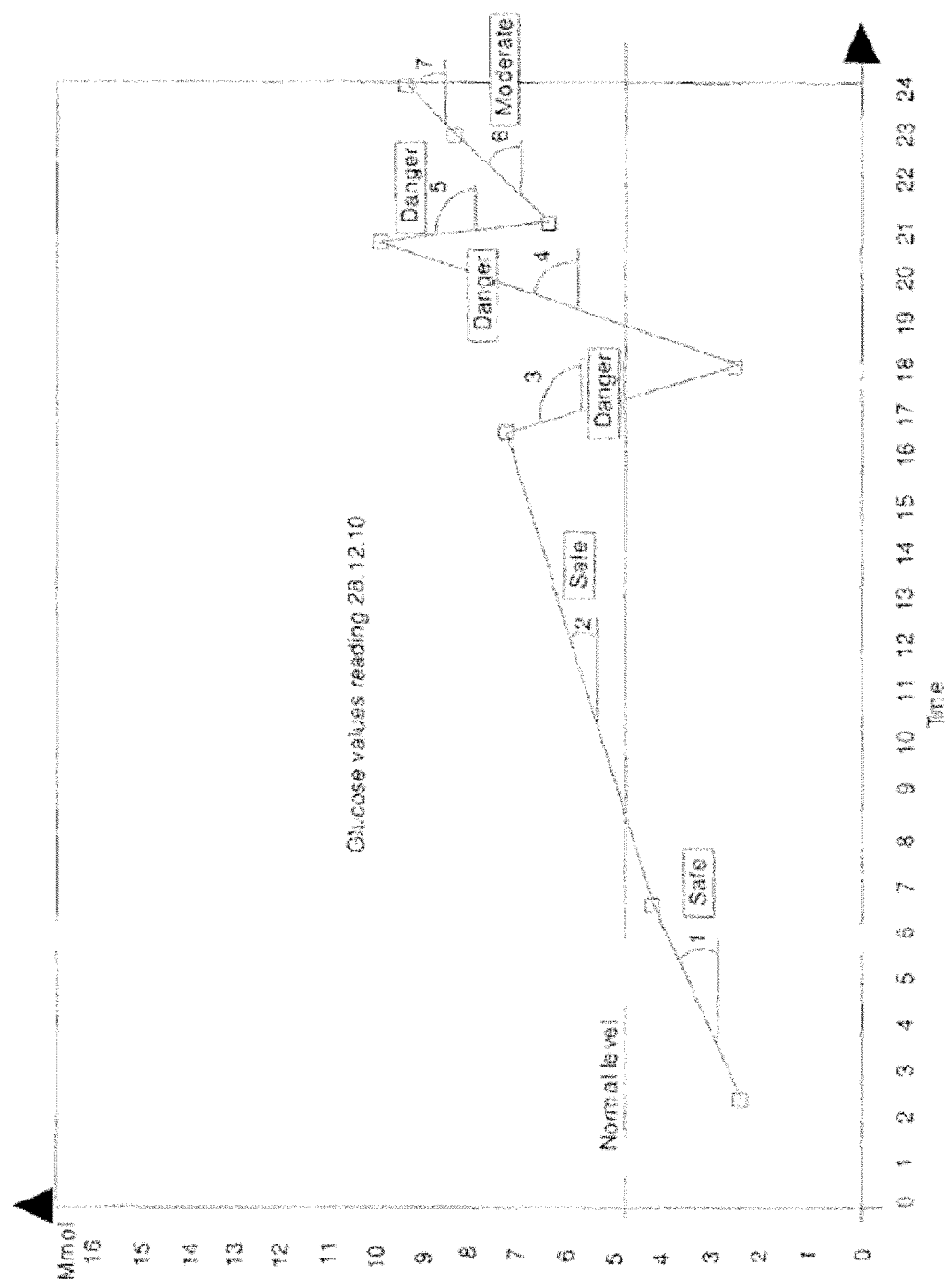
FIG. 15. Continuous monitoring of the development of glucose values.

In FIG. 15, the angles 1 and 2 show a moderate increase of the glucose values. At 17:00 o'clock the reading shows 7.2 mmol/l, but it was not possible to predict the value at 18:00 o'clock and not how fast it would drop to 2.4 mmol/l. With continuous monitoring, it would be possible to show the drop rate expressed by the angle 3 and thereby take action to prevent the fall towards hypoglycemia.

To accomplish this, we searched for other physical changes of the blood caused by the variations of the glucose level which could be detected without penetrating the skin.

The body fluid, in living humans and animals, contains thousands of different molecules and organisms, and where the concentration of some of these varies slowly whereas others can vary rapidly. The latter is the case for glucose in diabetics, lactic acid in human and animal athletes, cholesterol, virus, bacteria, loss of water etc. It is the concentration of all the molecules together with the property of the body liquid which gives the density of the said liquid with its solutes.

The object of the present invention is to make an instrument/sensor, which can be applied non-invasively for example on the ear lobe, and where a transducer transmits a pulse, or a pulse train such as vibrations into the body fluid.

The acceleration of a body is following Newton's second law $F=m*a$ (N) where m is the mass of the body in kg and a is the acceleration in m/s$^2$.

When applying a constant mechanical pulse into the fluid, one will have varying accelerations according to:

$$a_x = F/m_x \text{ (m/s}^2\text{)}$$

Where F is the constant pulse in N and $m_x$ is the varying mass,

If applying a constant acceleration, one will experience a varying force according to:

$$F_x = m_x * a \text{ (N)}$$

Where $m_x$ is the varying mass and a is the constant acceleration.

These variations can be picked up by different existing elements such as piezo electrical crystals, detection coils, silicon pressure transducers or accelerator meters, light diodes or other sensitive pick up instruments.

For normal diabetics, the density of the body fluid will be a measure of the changed level of glucose in the fluid and for athletes; a changed density can be a measure of an increased level of lactic acid. The same will apply for dehydration, as loss of water will concentrate the normal molecules and substances present in the body fluid.

The following table shows values of the glucose molecule.

| Avogrados number $N_A$ = | 6.02E+23 |
|---|---|
| | GLUCOSE a |
| Molecular weight M = g (Dalton) | 180 |
| Specific weight sg = g/cm3 | 1.544 |
| Volume of one mol V = M/sg = cm3 | 116.58 |
| Volume each molecule dV = V/$N_A$ = cm3 | 1.93655E−22 |
| Packing factor x = % | 47.6 |
| Diameter molecule D = (6 * V/3.14)$^{1/3*x}$ = cm | 1.50826E−07 |
| Diameter molecule D = Å = | 1.51 |
| Peritoneal concentration: | |
| mmoll/l | 5.00 |
| Mass mg/l | 900.00 |
| Mass g/l | 0.90 |
| Mass in an average body of 80 kg (l) = g | 72.00 |
| Osmotic pressure π = 2.58 Mo = (kPa) | 12.90 |
| Osmotic pressure p = 2.58 Mo = mbar | 129.00 |
| Molecular concentration mmol/l | 1 |
| Osmotic pressure p = mbar | 25.4 |

Figure 16:
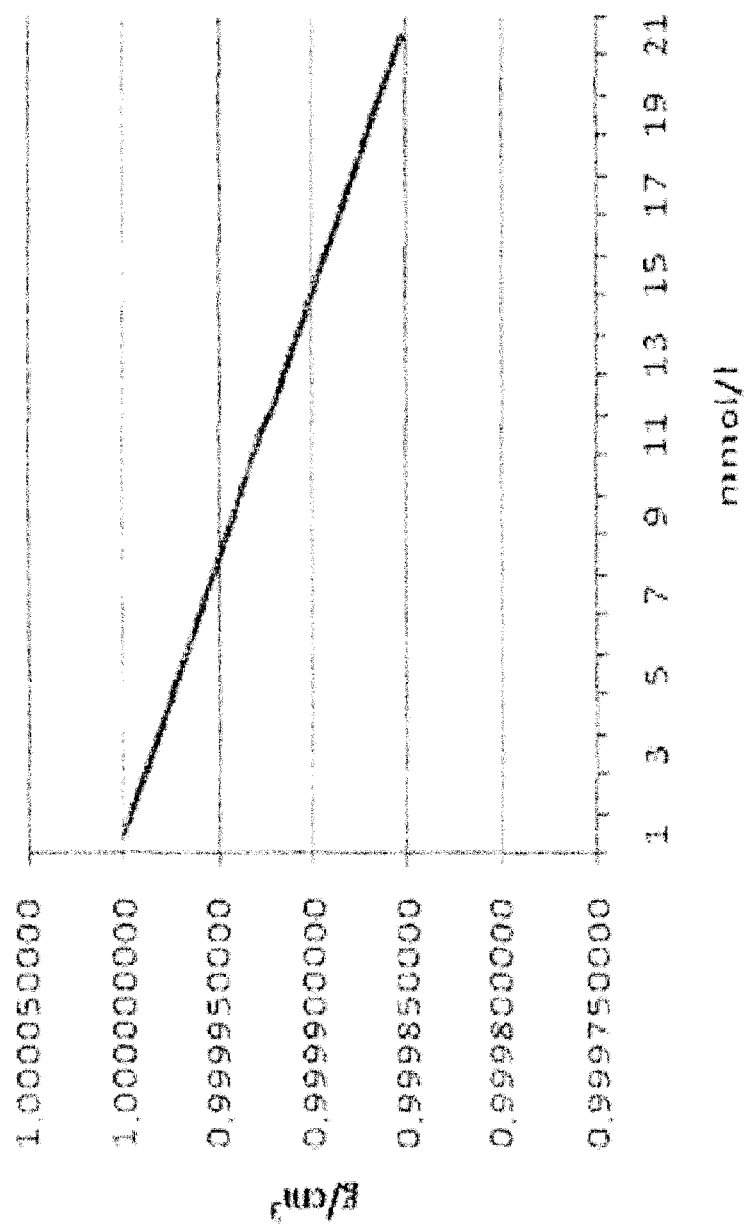
FIG. 16. Density of water with varying sugar content.

FIG. 16 shows the density variation in water caused by variations of glucose from 1 to 20 mmol/liter.

As can be seen, the variations are, as expected, linear. As the variations take place beginning after the fifth digit after comma, the sensor must have a high enough sensitivity to register these variations.

The density is, however, also dependent upon the temperature because of the expansion coefficient of the liquids which has to be taken into consideration and compensated for. The volume of a liquid expands by the following equation:

$$V_x = V_1 * (1+\mu(t_2-t_1)) \text{ (dm}^3\text{)}$$

Where is the reference volume in question, $\mu$=expansion coefficient which for water is $0.18*10^{-3}$, $t_2$ is the increase of the temperature and $t_1$ is the reference temperature. The general equation of the density is p=m/V where m is the mass for the given volume V. Thus for a mass m (kg) at the volume $V_1$ (the density will change by the equation:

$$P_x = m/Vx = m/(V_1*(\mu(t_2-t_1)) \text{ (kg/dm}^3\text{)}$$

Figure 17:
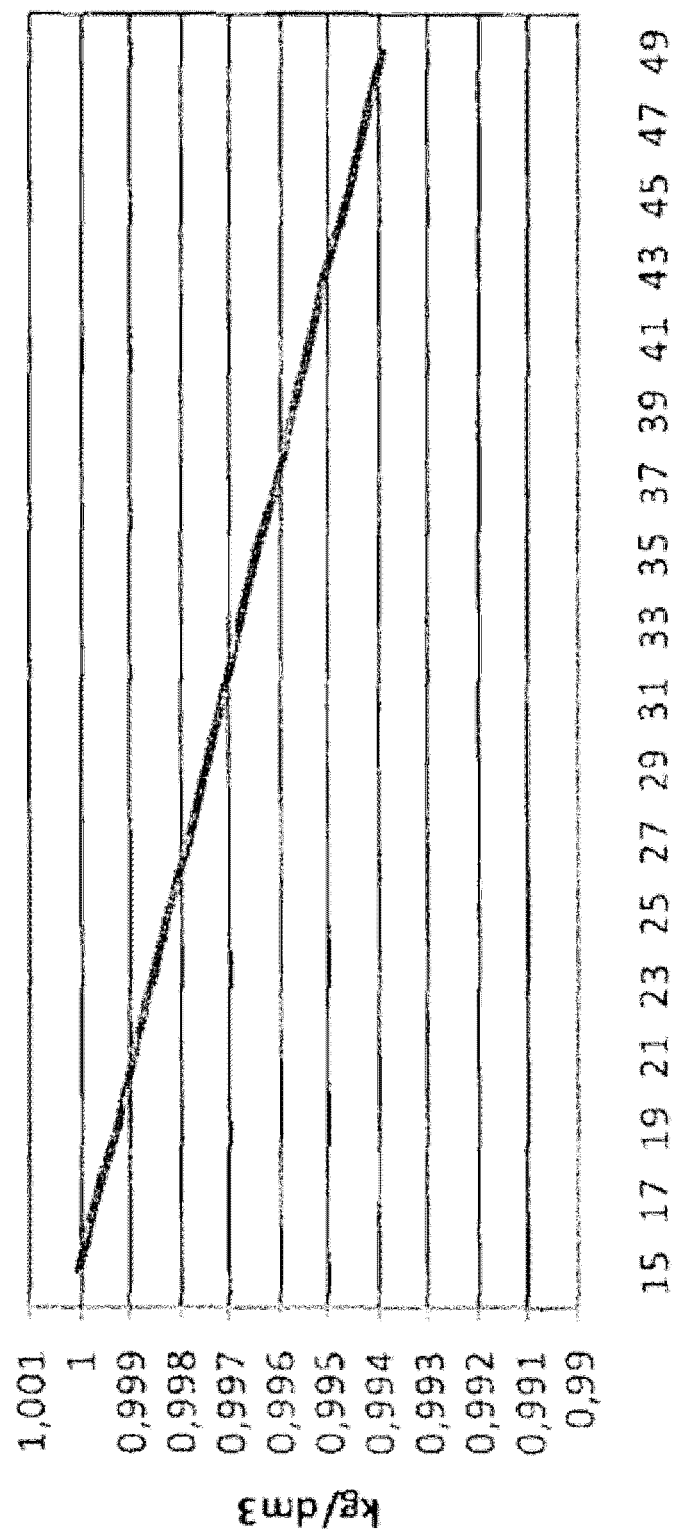
FIG. 17. Density of water versus temperature.

The variation of the density of water between 15 and 49 C is shown in the FIG. 17.

The variation of the density caused by the temperature is compensated by a mathematical algorithm in the processor which processes the recorded data from the pulse thereby giving the density at the temperature by the calibration of the sensor. The calibration of the sensor takes place by adjusting the set point at a glucose level given by a standard glucose meter whereby the set point of the temperature is automatically set by the thermometer incorporated in the sensor. From this set point, the sensor detects the variations caused both by the variation of the tension in the skin and the solutes in the body liquid and the temperature.

Figure 14:
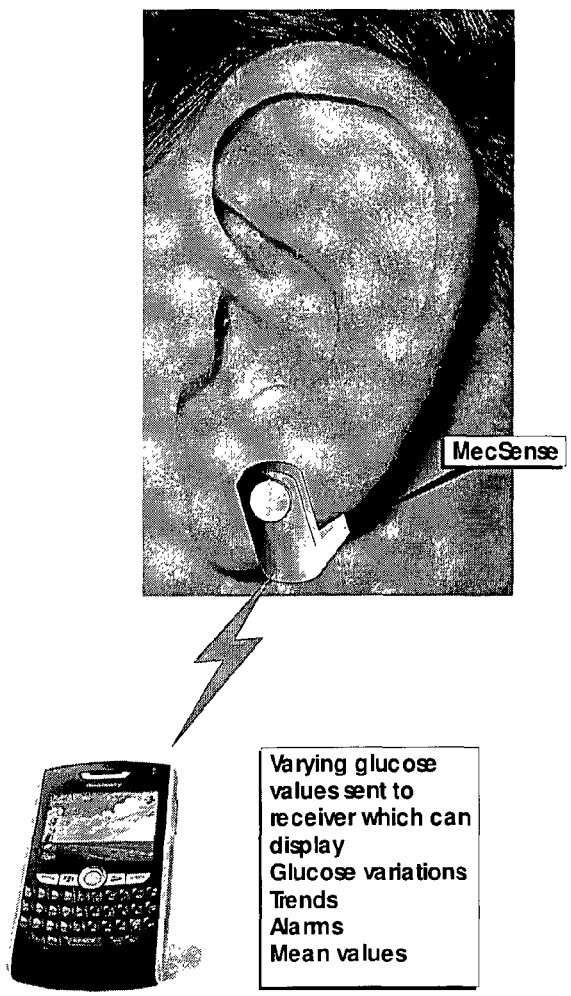
FIG. 14 Wireless transmission of data.

The present invention thus provides a sensor for measuring the density of a body liquid by generating a pulse or pulses that hits the skin and where a transducer will pick up the speed of the pulse which is dependent on the composition of the body fluid and the elasticity of the skin. The pulse may be a mechanical pulse, vibration or a compressed air/liquid pulse or any other means of a pulse like a sound wave that will be recorded by a pickup device that may be a pickup coil, microphone, silicone pressure transducer, stretch pad, accelerator meters, light diodes or other sensitive instruments. A temperature sensor touching the skin will continuously record the temperature close to the area where the pulse hits the skin, the transducer delivers the results to a microprocessor or an ASIC that has an algorithm that calculates the relative density which is dependent on the composition of the fluid. One such substance which causes rapid variation of the body fluids composition is its content of glucose. The results of the readings caused by the variation of the glucose content are therefore an estimate of the glucose level. The glucose data can be transmitted wirelessly or by wire to an external receiver where the readings are shown on a display as glucose values expressed in mmol per liter or any other unit, such as mg per liter (see FIG. 14). The sensor may have alarms for high and low glucose levels. Since the sensor device has to be calibrated by the user by using a standard glucose sensor, the sensor may receive this calibration with Bluetooth making the user able to send the calibration data by cell phone. The cell phone may also be the device used for displaying the glucose data. The microcontroller or the ASIC in the glucose sensor is programmed to interpret input data like calibration data or other data that makes it respond to glucose values with an underlying text. The receiving device will have a keyboard making the user able to send information to the glucose sensor and the software needed to do so.

The software that handles the data sent from the above mentioned glucose sensor includes alternative display of the signals (digits or graphs), warning signals and different computing of historical data such as mean values of the glucose level, the rate of which the values raise and falls. In the case of hypo/hyperglycemia, an alarm will go off at preset points. The same is the case if the rise and fall rate is faster or slower than preset values. If the temperature is too high, a warning text preferably informs the user that the displayed value may be wrong if the user is suffering from dehydration and or low salt level. The user can also add information about exercise and what kind of food he or she will eat in addition to the amount of insulin and type of insulin injected or tablets, so that the glucose values becomes understandable. Preferably the software may deliver comments and suggestions of what to do.

The present invention also provides a sensor for measuring the resistance of a membrane, such as skin, having a complex or single fluid on one of its sides, caused by the change of the membrane and the fluid characteristics caused by variation of the membrane elasticity and the fluid composition. Such as that observed by varying glucose level in diabetics and lactic acids in humans and animals, by measuring the acceleration or pressure variations of the membrane and the body fluids in accordance with Newton's second law with a mechanical pulse and/or vibrations applied to the tissue which can be the ear lobe. Variations of the body fluids density and the membranes elasticity gives a measure of the variations of the membranes elasticity and the concentration of solutes in the fluids to be recorded from a set value.

According to the present invention the mechanical pulse can be generated by an electromagnet with an iron core which is made magnetic when energizing the electro magnet and where the pulse body can be a permanent magnet having the same pole as the pole in the iron rod, which causes the permanent magnet to be repelled from the iron core. The pulse can also be generated by a magnetostrictive material which expands under the influence of a magnetic field. The detection of the pulse can be recorded by a detection coil or by a variable capacitor.

Another way to implement the present invention would be to apply a vibrating force to the membrane where the damping of the vibrations and its amplitudes is dependent upon the attenuation of the fluid which is caused by the variations of the density of the body fluids and the membrane's elasticity. The amplitudes will give a measure of the variations of the membrane's elasticity and the concentration of solutes in the fluids to be recorded from a set value and which is shown as variation of the glucose level either in mmol/liter or mg/dl or any other unit.

The vibration force may be generated by a magnetic or piezo electric vibrator and the amplitudes of which can be detected either with a small self inducing linear or circular generator or any other receiver, such as a microphone which can detect variations of the changed amplitudes caused by the changed elasticity of the membrane caused by variations of the composition of the liquid on one of its sides.

The present invention also provides a structure for a sensor for measuring at least one property of a tissue object, the structure comprising first and second elongate carriers being connected at respective base sections thereof and extending there from in substantially same directions, and having means for clamping respective first sections of the first and second elongate carrier sections located distally from the base sections, to respective opposite sides of the tissue object, wherein the first carrier carrying in the first section thereof a first transducer having an excitation input and comprising an actuator having a movable element being arranged to be accelerated in a direction of the first section of the second carrier in response to excitation energy provided to the excitation input, so as to be capable of delivering at least part of the excitation energy to the tissue object, and the second carrier carrying in the first section thereof a second transducer having a signal output and comprising a pick-up being arranged to be accelerated in a direction of the first section of the first carrier for providing energy at the signal output in response to acceleration of the movable element, so as to be capable of delivering on the signal output a receive signal including at least part of excitation energy picked up from the tissue object.

In a preferred embodiment of the present invention the sensor comprises the above structure, and transceiver and signal processing circuitry are coupled to the excitation input and the signal output, and are arranged a) to provide the excitation energy in form of a single pulse, a pulse train or variation, according to a predetermined temporal pattern, b) to prepare and store receive signal data, and c) to process stored receive signal data with respect to the temporal pattern to determine the variation.

Figure 1:
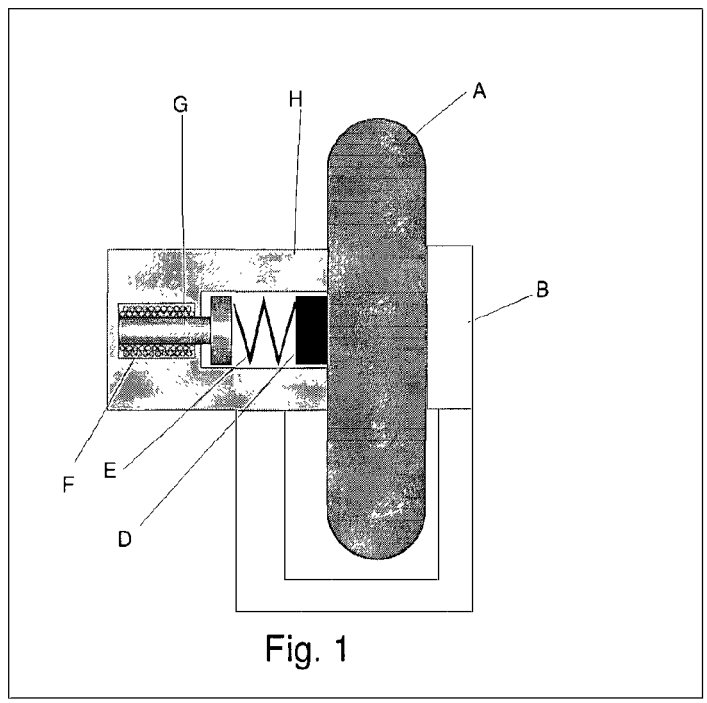
FIG. 1 illustrates an embodiment of the invention wherein a constant pulse is used.

FIG. 1 illustrates an instrument with a constant pulse F. The instrument consists of a housing H which is built up with a second body B having a clamping device, body H which houses the coil F with its iron rod G and a variable resistor or capacitor E attached to an impact body D. When applying a current pulse from a power source to the coil, it will accelerate the iron rod against the resistor or capacitor connected to the impact body against the ear lobe A. The different densities will give different readings of the variable resistor or condenser and where the readings can be given in values for the glucose level. The instrument must be calibrated before use, which is done by measuring the glucose level with a standard glucose meter. By the shown value of the glucose level, the instrument will show varying readings from the set point.

Figure 1A:
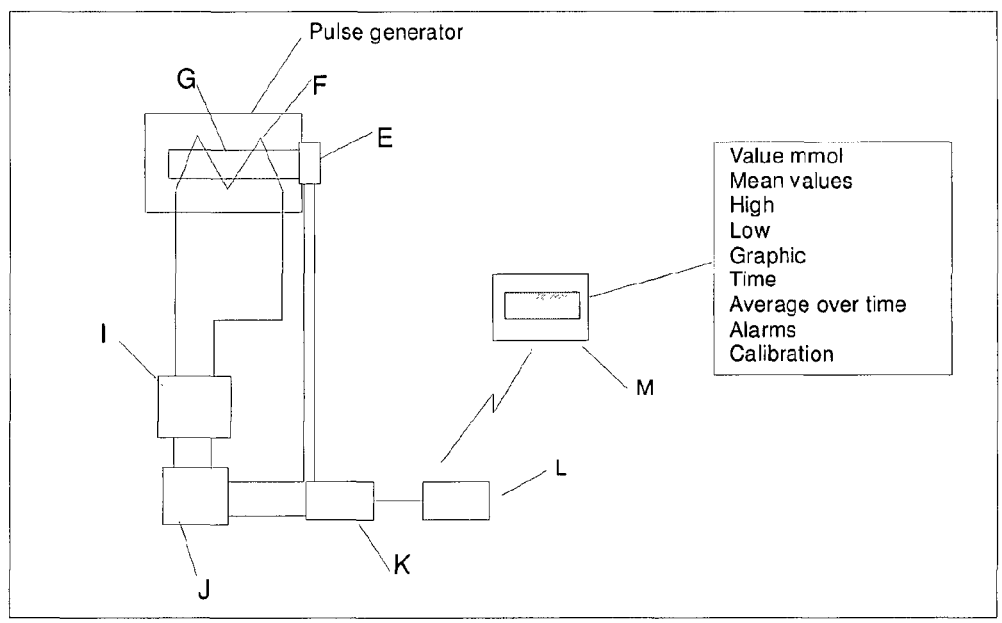

FIG. 1A shows the wiring diagram for this solution where I is a timer which reads the impulse time, J is a power source which rapidly discharges a current to the coil. The discharged power is the same for each pulse and this can be accomplished by discharging the current from a loaded capacitor. E is the variable resistor or capacitor which detects the force from the activated rod. The force is transmitted to a microprocessor K which computes the signal and transmits it to a sender L which transmits the signal either wirelessly or by wire to a receiver M which shows the detected signal as variations from the set point. If a premeasured glucose level was say 5 mmol/liter, the shown impulse value at that glucose level is shown as the same value for whatever value the impulse gave, for example x. By a value of x+z, this shows a figure value higher than 5.

Figure 2:
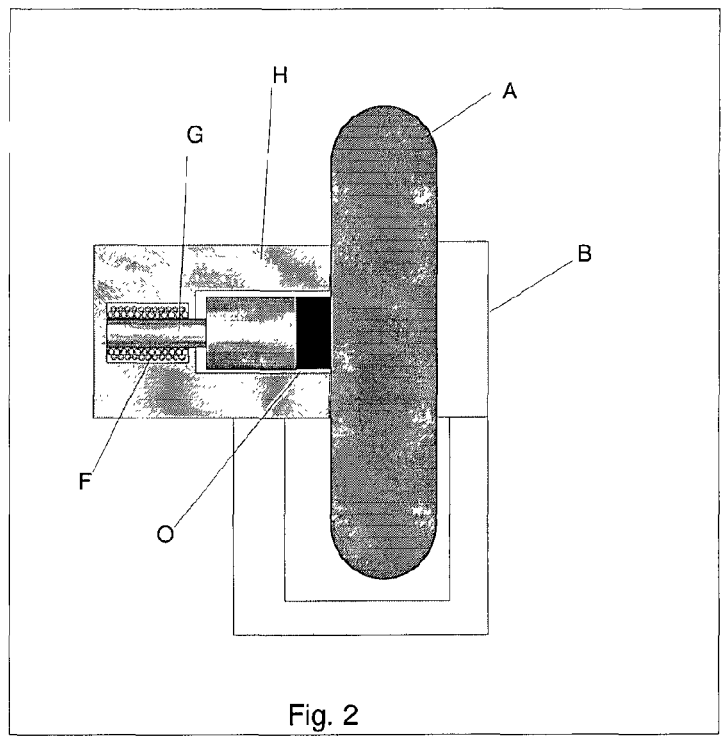
FIG. 2 shows the wiring diagram for the embodiment of FIG. 1.

FIG. 2 shows an instrument as in FIG. 1, but where the variable resistor or capacitor is replaced with a silicon pressure transducer or a silicon accelerometer O which picks up the pressure or acceleration generated by the constant pulse.

The pulse will be accelerating the transducers against the skin and the pressure recorded is dependent upon the density of the displaced tissue. When using an accelerometer, the acceleration is dependent upon the mass of the displaced tissue—in both cases; the density is a function of the glucose content.

The wiring diagram will be similar to the wiring diagram FIG. 1A.

Figure 3:
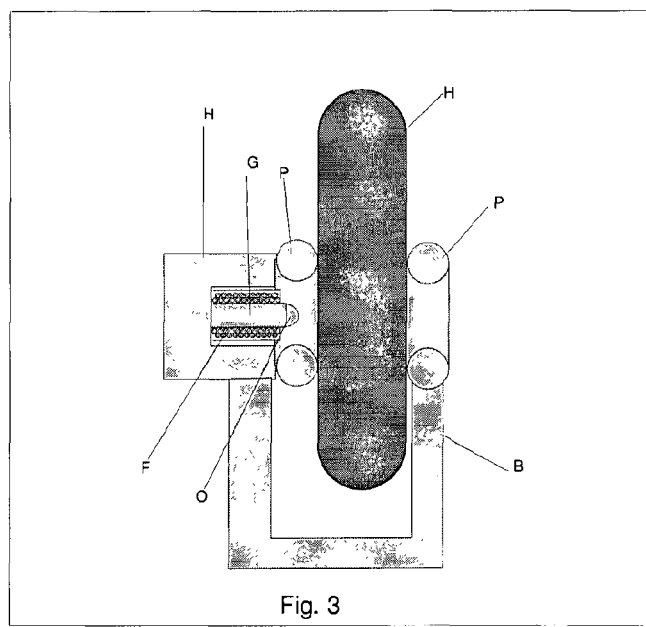
FIG. 3 illustrates another embodiment of the invention.

FIG. 3 shows still another layout where the ear lobe support on both sides are ring shaped P and where the impact part (pressure transducer) on the iron rod in resting position does not touch the skin before the pulse generator is activated. It is to be understood that the impulse generator can be any kind of a rapid accelerator such as a piezo electrical pulse generator where it is the expansion of the piezo electrical crystal which gives the mechanical movement. The piezo electrical crystal can also be replaced with another material which expands under the influence of a magnetic field, such as Terfonol which is an alloy of Terbium, Dysprosium and Ferrum. The wiring diagram will more or less be as for FIG. 1.

It is to be understood that the principle can be applied to any configuration which can be given by Newton's laws.

The recorded data can be sent to a hand held instrument, such as a cell phone by BLUETOOTH®.

Figure 4:
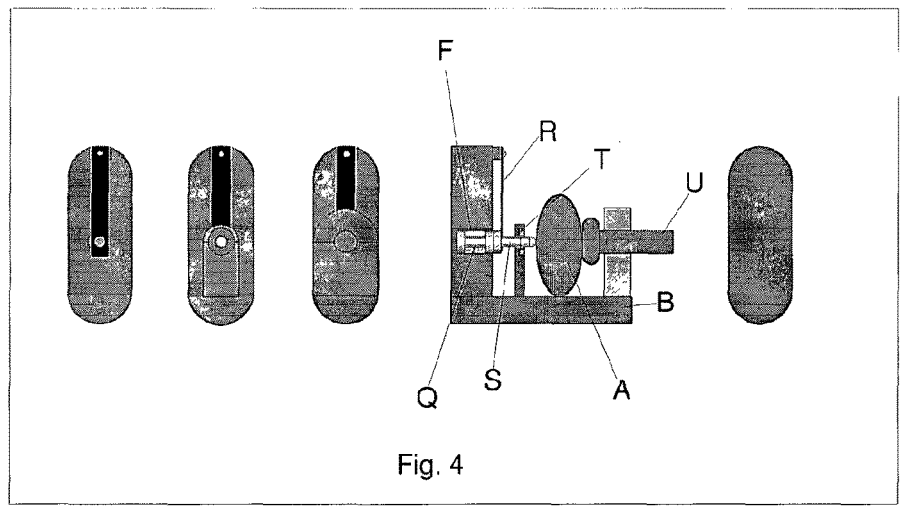
FIG. 4 shows a further variation of the embodiment of FIG. 1.
Figure 4A:
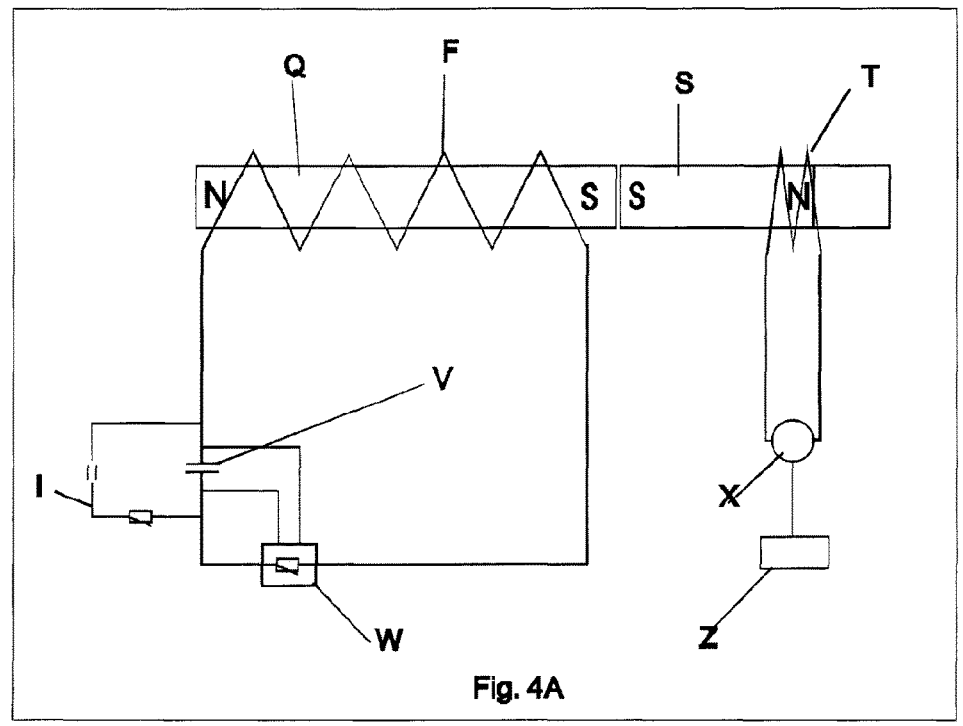

FIG. 4 shows an example of the lay-out in accordance with FIG. 1 and FIG. 4A shows the associated wiring diagram of FIG. 4.

A movable permanent magnet S is given a magnetic impulse generated by activation coil F having a fixed and not movable iron core Q. As the moveable magnet is moving, its one pole will, in a detection coil T, create a current in the coil where the values voltage and current (V and I) are dependent upon the velocity of the magnet which in turn is dependent upon the resistance in the end of the magnet caused by variation of the density of the displaced fluid in the ear lobe. In order to have the same mechanical resistance of the moveable magnet, it is shown attached to a flexible spring R, which maintains its elastic properties over time. The tension of the sensor against the ear lobe is adjusted by the screw device U.

FIG. 4A shows the wiring diagram of FIG. 4 with the power source I and the capacitor V which is opened for charge drainage by the resistor W. The detection coil is shown as T, where the generated current is detected by the current detector X and which values are shown in the reader Z.

FIG. 5 shows the practical lay-out of the pulse generator, and FIG. 6 shows the pulse shape generated from the pulse generator.

The following calculations can be shown as an illustration of the principle:

| | | |
|---|---|---|
| Bacic equation F = m * a | | N |
| m = mass to be accelerated | | kg |
| a = acceleration | | m/s$^2$ |
| A constant pluse with a constant force, gives a variable acceleration which varies with m | | |

| ASSUMPTIONS | | | |
|---|---|---|---|
| Diameter of fluid droplet d = | | 3 m.m. = | 0.03 dm |
| Volume of fluid droplet | 0.00001413 dm3 | | |
| V = d$^3$ * 3.14/6= | | | |
| Mass of droplet dm$_x$ = V * sg$_x$ = | | | |
| Impact length s = | | 0.25 m.m. = | 0.00025 m |
| Variable acceleration | | m/s$^2$ | |
| a$_x$ = F/m$_x$ = | | | |
| Force F = | | 0.00001 N | |
| Travel time t$_x$ = 2 * s * m$_x$/F = | | s | |
| Acceleration a$_x$ = 2 * s/t$_x^2$ = | | m/s$^3$ | |
| Impulse time dT = | | 1 ms = | 0.001 s |
| Velocity at end of pulse v = a$_x$ * t$_x^2$/2 = | | | 0.5000 m/s |

The result of the calculations are shown below.

| Density of glucose 0.961 kg/dm3 = 0.961 g/cm3 | | | | | |
|---|---|---|---|---|---|
| Glucose conc. | Weight of glucose Gg (gr) | | Volum water cm$^3$ | Weight of Water Gw (gr) | Total Weight Gx = Gg + Gw gr |
| 0 mmol/l = | 0 mg/l = | 0 g/l = | 0 cm3 | 1000 | 1000 | 1000 |
| 1 mmol/l = | 180 mg/l = | 0.18 g/l = | 0.18770489 cm3 | 999.8126951 | 999.8126951 | 999.8126951 |
| 2 mmol/l = | 360 mg/l = | 0.36 g/l = | 0.37460978 cm3 | 999.6253902 | 999.6253902 | 999.6253902 |
| 3 mmol/l = | 540 mg/l = | 0.54 g/l = | 0.56191467 cm3 | 999.4380853 | 999.4380853 | 999.4380853 |
| 4 mmol/l = | 720 mg/l = | 0.72 g/l = | 0.74921956 cm3 | 999.2507804 | 999.2507804 | 999.2507804 |
| 5 mmol/l = | 900 mg/l = | 0.9 g/l = | 0.93652445 cm3 | 999.0634755 | 999.0634755 | 999.0634755 |
| 6 mmol/l = | 1080 mg/l = | 1.08 g/l = | 1.12382934 cm3 | 998.8761707 | 998.8761707 | 998.8761707 |
| 7 mmol/l = | 1260 mg/l = | 1.26 g/l = | 1.31113424 cm3 | 998.6888658 | 998.6888658 | 998.6888658 |
| 8 mmol/l = | 1440 mg/l = | 1.41 g/l = | 1.49843913 cm3 | 998.5015609 | 998.5015609 | 998.5015609 |
| 9 mmol/l = | 1620 mg/l = | 1.62 g/l = | 1.68574402 cm3 | 998.314256 | 998.314256 | 999.934256 |
| 10 mmol/l = | 1800 mg/l = | 1.8 g/l = | 1.87304891 cm3 | 988.1269511 | 988.1269511 | 999.9269511 |
| 11 mmol/l = | 1980 mg/l = | 1.98 g/l = | 2.0603538 cm3 | 997.9396462 | 997.9396462 | 999.9196462 |
| 12 mmol/l = | 2160 mg/l = | 2.16 g/l = | 2.24763869 cm3 | 997.7523413 | 997.7523413 | 999.9123413 |
| 13 mmol/l = | 2340 mg/l = | 2.34 g/l = | 2.43496358 cm3 | 997.5650364 | 997.5650364 | 999.9050364 |
| 14 mmol/l = | 2520 mg/l = | 2.52 g/l = | 2.62226847 cm3 | 997.3777315 | 997.3777315 | 999.8377315 |
| 15 mmol/l = | 2700 mg/l = | 2.7 g/l = | 2.80957336 cm3 | 997.1904266 | 997.1904266 | 999.8904266 |
| 16 mmol/l = | 2680 mg/l = | 2.88 g/l = | 2.99687825 cm3 | 997.0031217 | 997.0031217 | 999.8331217 |

-continued

| | | | | | | | |
|---|---|---|---|---|---|---|---|
| 17 | mmol/l = | 3060 mg/l = | 3.06 g/l = | 3.18418314 cm3 | 996.8158169 | 996.8158169 | 999.8758169 |
| 18 | mmol/l = | 3240 mg/l = | 3.24 g/l = | 3.37148803 cm3 | 996.628512 | 996.628512 | 999.868512 |
| 19 | mmol/l = | 3420 mg/l = | 3.42 g/l = | 3.55879292 cm3 | 996.4412071 | 996.4412071 | 999.8612071 |
| 20 | mmol/l = | 3600 mg/l = | 3.6 g/l = | 3.74609781 cm4 | 996.2539022 | 996.2539022 | 999.8539022 |

| | | | Weight | By constand a | By contant F | |
|---|---|---|---|---|---|---|
| Glucose conc. | Density $sg_x$ | | dropplet gr | Fx (N) | tx (s) | $a_x = 2 * s/t_c^2$ |
| 0 | 1.000000000 g/cm3 | | 0.014130000 | 0.007065000 | 0.00070650000 | 1001.71845 |
| 1 | 0.999992695 g/cm3 | | 0.014129897 | 0.007064948 | 0.00070649484 | 1001.73308 |
| 2 | 0.999985390 g/cm3 | | 0.014129794 | 0.007064897 | 0.00070648968 | 1001.74772 |
| 3 | 0.999973085 g/cm3 | | 0.014129690 | 0.007064845 | 0.00070648452 | 1001.76235 |
| 4 | 0.999970780 g/cm3 | | 0.014129587 | 0.007064794 | 0.00070647936 | 1001.77699 |
| 5 | 0.999963476 g/cm3 | | 0.014129484 | 0.007064742 | 0.00070647420 | 1001.79163 |
| 6 | 0.999956171 g/cm3 | | 0.014129181 | 0.007064690 | 0.00070646903 | 1001.80626 |
| 7 | 0.999948866 g/cm3 | | 0.014129277 | 0.007064539 | 0.00070646387 | 1001.8209 |
| 8 | 0.999941561 g/cm3 | | 0.014129174 | 0.007064587 | 0.00070645871 | 1001.83554 |
| 9 | 0.999934256 g/cm3 | | 0.014129071 | 0.007064536 | 0.00070645355 | 1001.85017 |
| 10 | 0.999926951 g/cm3 | | 0.014128968 | 0.007064484 | 0.00070644839 | 1001.86481 |
| 11 | 0.999919646 g/cm3 | | 0.014128565 | 0.007064432 | 0.00070644323 | 1001.87945 |
| 12 | 0.999912341 g/cm3 | | 0.014128761 | 0.007064381 | 0.00070643807 | 1001.89409 |
| 13 | 0.999905086 g/cm3 | | 0.014128658 | 0.007064329 | 0.00070643291 | 1001.90873 |
| 14 | 0.999897732 g/cm3 | | 0.014128555 | 0.007064277 | 0.00070642775 | 1001.92337 |
| 15 | 0.999890427 g/cm3 | | 0.014128452 | 0.007064226 | 0.00070642259 | 1001.93801 |
| 16 | 0.999883122 g/cm3 | | 0.014128349 | 0.007064174 | 0.00070641743 | 1001.95265 |
| 17 | 0.999875817 g/cm3 | | 0.014128245 | 0.007064123 | 0.00070641226 | 1001.96729 |
| 18 | 0.999868512 g/cm3 | | 0.014128142 | 0.007064071 | 0.00070640710 | 1001.98193 |
| 19 | 0.999861207 g/cm3 | | 0.014128039 | 0.007064019 | 0.00070640194 | 1001.99657 |
| 20 | 0.999853902 g/cm4 | | 0.014127936 | 0.007063968 | 0.00070639678 | 1002.01121 |

Yet another principle to detect the variation of the combined resistance from a membrane and its associated liquid is to apply a vibrating force on a body connected to the ear lobe. By applying vibration force to the body, its damping will depend on flexibility of the membrane, here the skin, and the physical properties of the body liquid. As the density of the liquid changes, the amplitude of the vibrations will increase by increasing density and vice versa and is thus a value of the varying resistance of the ear lobe.

Figure 7:
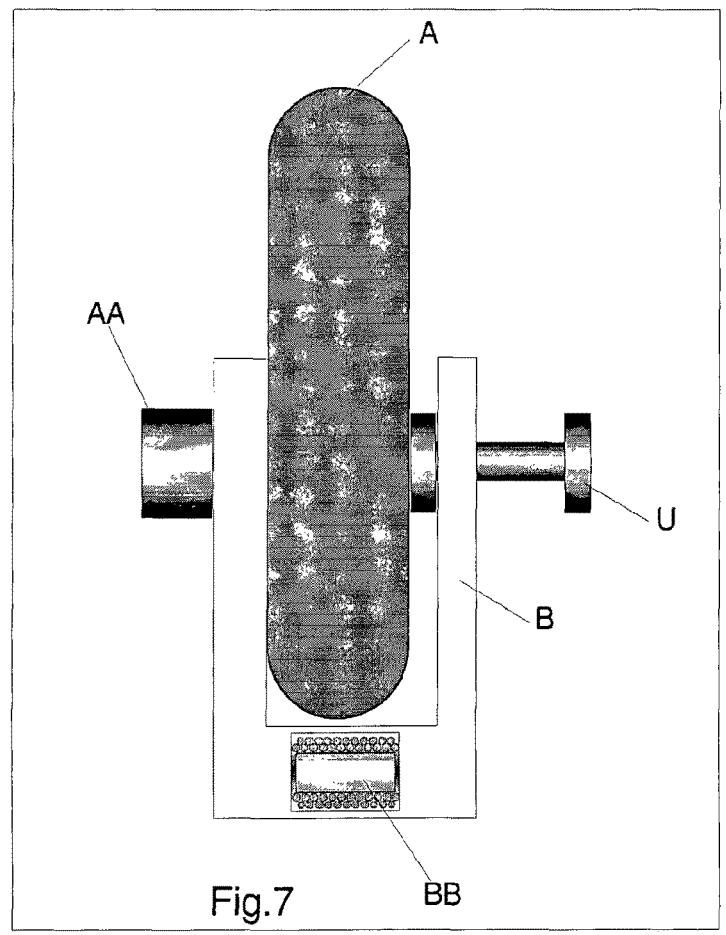
FIG. 7 illustrates another embodiment of the present invention.

FIG. 7 shows an example of this principle where an U-shaped body B is connected to an ear lobe A, having a frequency controllable vibrator AA and a generator BB which consists of a magnet core surrounded by a coil. When the vibrator is activated, the body, such as the ear lobe, comes into vibrations and accelerates the magnetic core. The accelerations of the core is dependent upon the amplitude of the vibrations which again is dependent upon the damping of the vibrations caused by the variations in the body fluid.

Figure 8:
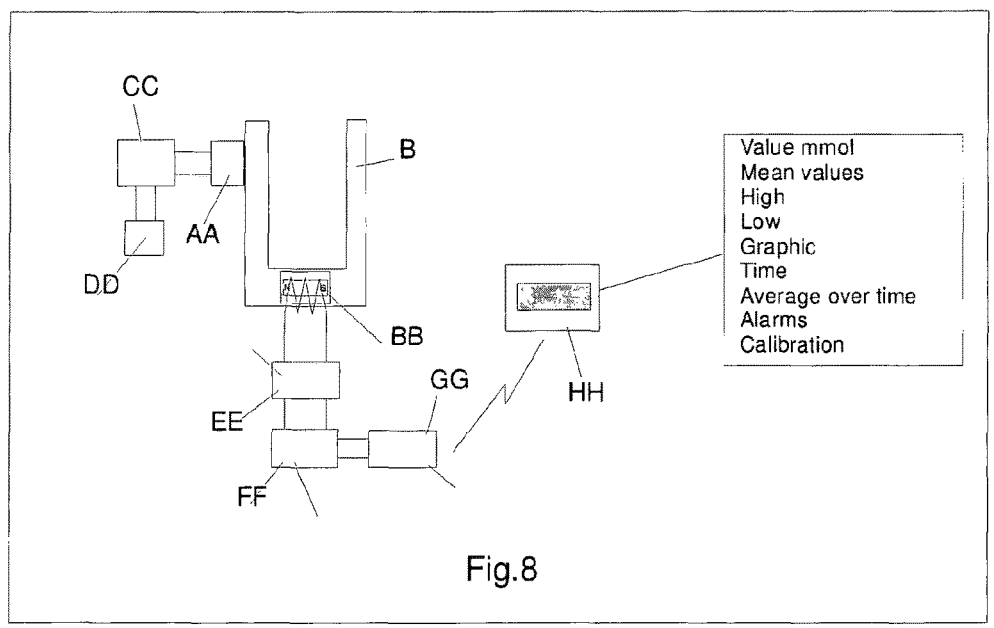
FIG. 8 shows the principle layout of the wiring diagram of FIG. 7.

FIG. 8 shows the principle layout of the wiring diagram of FIG. 7.

CC is a power source which activates the vibrator AA, and its frequency is controlled by a frequency controller DD. The generator BB is connected to an ampere meter EE which passes the recorded current values to a microprocessor FF which computes the values and by wire or wirelessly by GG sends the values to the receiver HH which presents the values of the variations of the vibrations in numbers from a preset point, as explained above.

Figure 9:
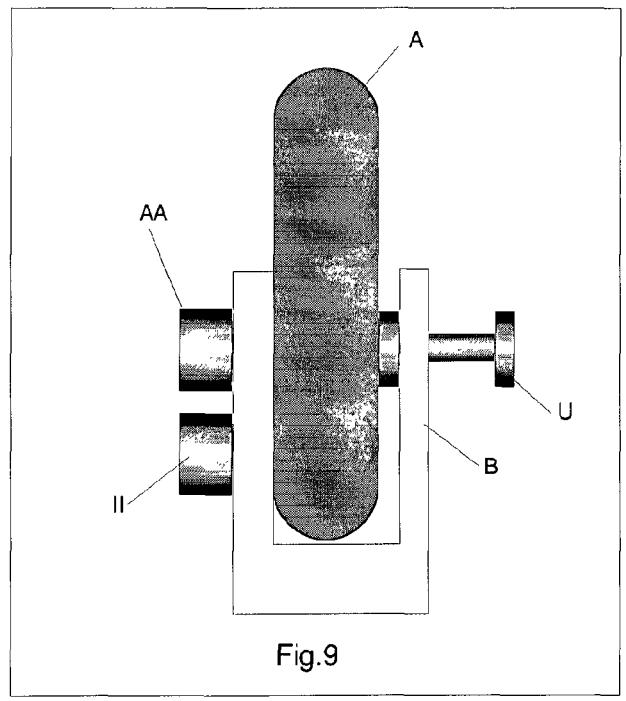
FIG. 9 illustrates a variation of the principle shown in FIG. 7.

FIG. 9 shows the same principle as shown in FIG. 7, but where the generator is replaced by a microphone II attached to the body detecting the variations of the amplitude.

Figure 10:
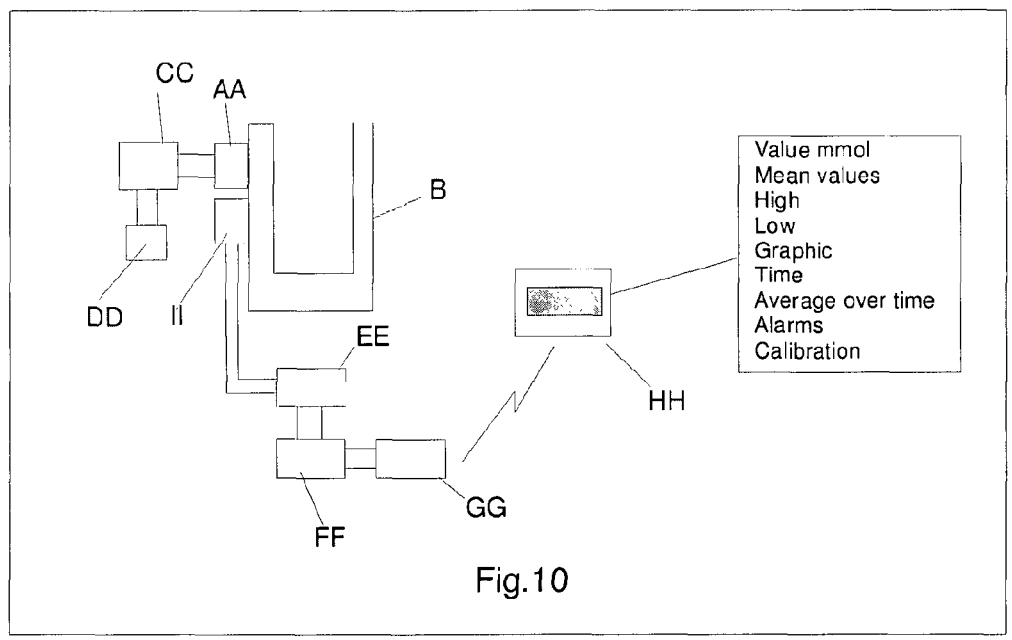
FIG. 10 shows the wiring diagram for the embodiment of FIG. 9.

FIG. 10 shows the principle layout of the wiring diagram for FIG. 9.

There exist a number of patents which utilize acceleration versus density to record a property of a solid, gas or liquid. U.S. Pat. No. 2,358,374 shows an instrument for measuring the density of a liquid and/or gas by means of a vibrating body (vane) immersed in a liquid. We are not immersing any body in the fluid itself, but applying a pulse or vibration on a membrane separating the fluid, i.e. the skin on living humans or animals.

The objective of the present invention is not to give a figure of the actual density of the fluid, but to show the variation of the fluids density, the membranes elasticity and viscosity caused by the change of composition of the fluid either it being the density or viscosity which both contribute to give a distinct signal of the resistance the sensor senses as described above. As stated above, the sensor needs to be calibrated by measuring the glucose content by a standard glucose sensor whereby the sensor will detect the variation from the set point. For example, if the measured glucose level is 5.5 mmol, whatever signal the sensor is given, this signal is set to be 5.5 mmol and any changes from this value will vary from this set point.

Figure 11:
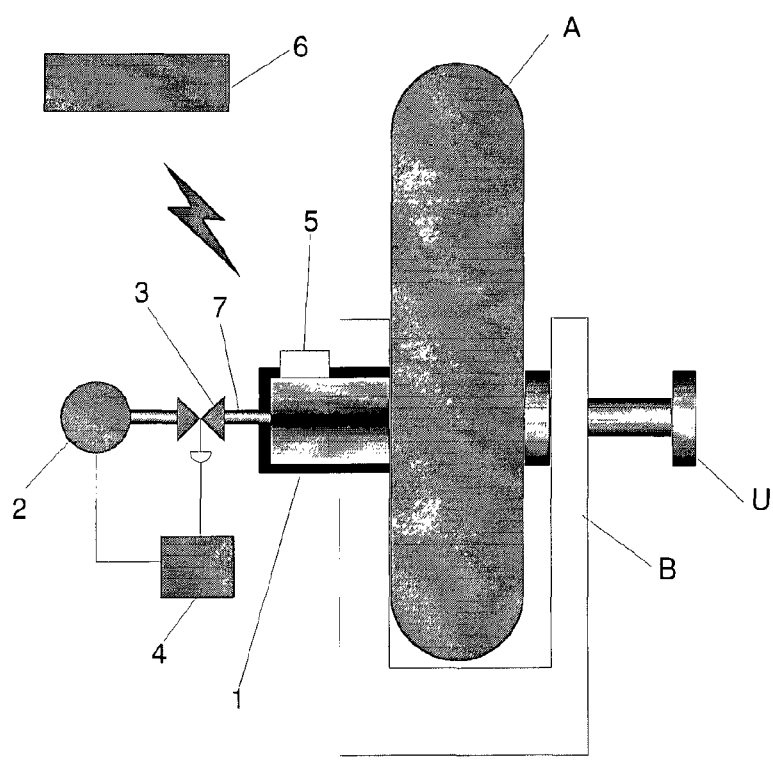
FIG. 11 shows still another embodiment of the present invention.

Still another means to generate a pulse which can be used according to the principle of the invention as described herein, is to use an air pulse as illustrated in FIG. 11.

Shown is a body B) attached to the ear lobe A) having a hollow body 1) connected to a pipe 7) and a rapid releasing valve 3) connected to an air source 2) which can be a micro compressor or another suitable means to compress air. On the hollow body 1) is attached a pressure sensor 5) having incorporated a temperature sensor and electronics for transferring values to an external reader 6). When the pressure in the air source 2) has reached a preset pressure, the pressure is detected by a pressure detector 4) which transmits a signal to the valve 3) to open, thus letting an air pulse to escape into the hollow body 1) and towards the air lobe. The compression of the air pulse will be dependent upon the elasticity of the skin and the underlying tissue with its fluid content which density is dependent upon the concentration of the fluid solutes.

The pressure is detected by the pressure transducer 5). As the pressure pulse can be affected by the surrounding temperature, a microprocessor attached to the transducer 5) or on the body B), compensates the signal by the recorded temperature to a preset mean temperature for the system.

A further application of the principles can be obtained by using vibration force where the amplitude of the vibrations also follows Newton's first law and where the damping of the vibrations is dependent upon the attenuation of the fluid which again is dependent upon its dissolved solutes and thereby its density.

This vibration principle can also be incorporated in other housings such as a ring on a finger.

Figure 12:
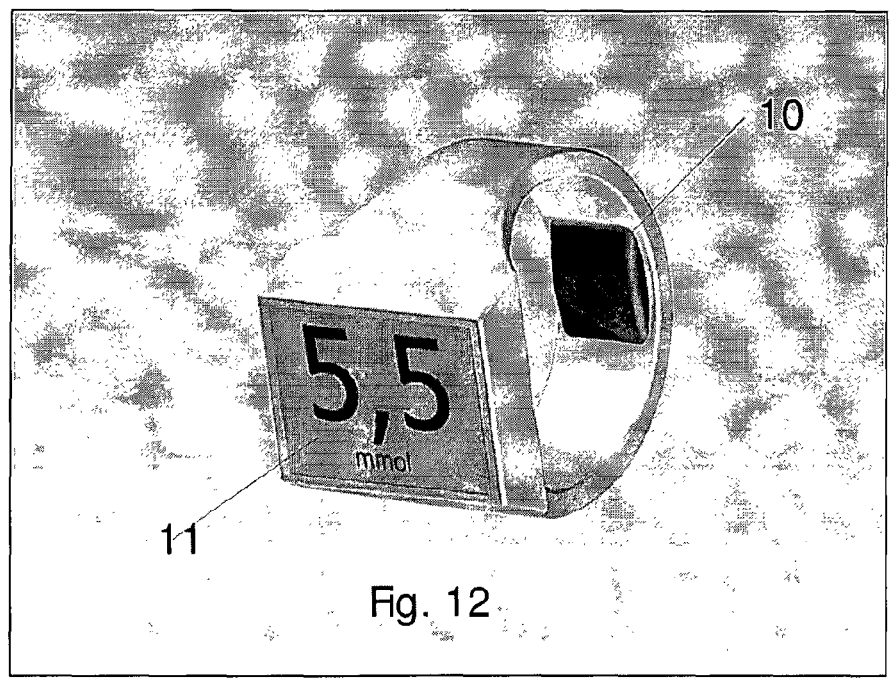
FIG. 12 illustrates an embodiment of an instrument incorporating the present sensor.

FIG. 12 shows a layout of the principle when using a pulse impact body shown as a pillow 10) inside the ring and where 11) is a display showing the read out value from the processor and power source located under the display.

Figure 13:
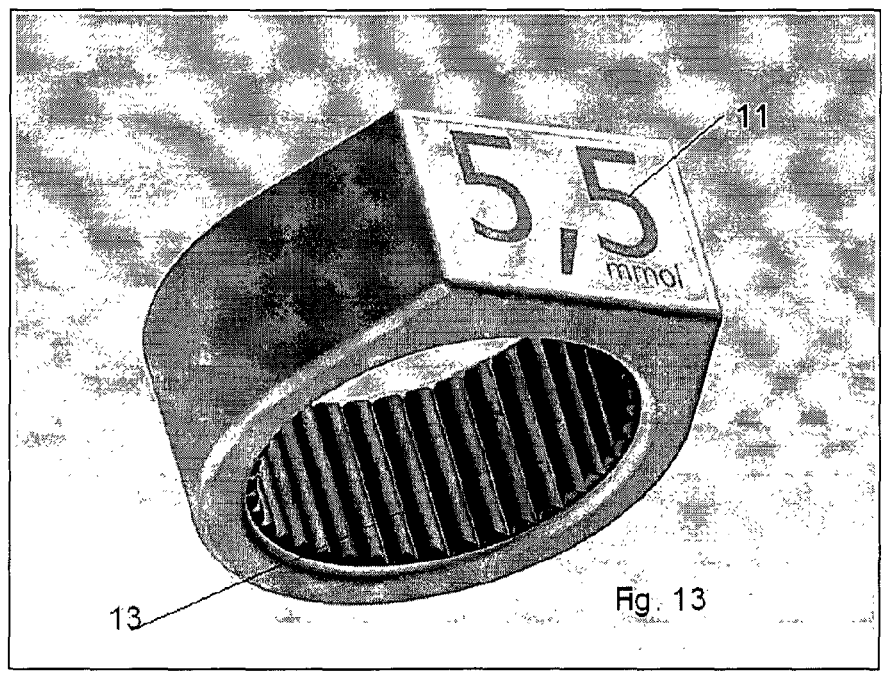
FIG. 13 illustrates another embodiment of an instrument incorporating the sensor according to the invention.

FIG. 13, shows a layout with a vibration source 13) arranged as a number of vibrating elements inside a ring and with the display and the associated electronics arranged as in FIG. 12.

The use of vibration force can be applied by any design of the sensors and for any location of the same, for example on the ear lobe.

Having described preferred embodiments of the invention it will be apparent to those skilled in the art that other embodiments incorporating the concepts may be used. These and other examples of the invention illustrated above are intended by way of examples only and the actual scope of the invention is to be determined from the following claims.

The invention claimed is:

1. A non-invasive sensor for measuring the density of a body fluid in contact with human skin comprising a single pulse generator, a temperature sensor and a transducer configured to register the speed of the pulse as a function of the body fluid and the elasticity of the skin when applying a constant force F, wherein said transducer is connected to a microprocessor in which a signal from the transducer is compensated by the recorded temperature to a preset mean temperature and transformed into values for the relative density of said body fluid and membrane elasticity, wherein the speed of the pulse is dependent on the composition of the body fluid and the elasticity of the skin, and the relative density is dependent on the composition of the body fluid.

2. The sensor of claim 1, wherein the pulse generating device generates a pulse in a form of a mechanical pulse, a vibrating force, or a compressed air/liquid pulse.

3. The sensor of claim 2, wherein the pulse generating device generates a mechanical pulse.

4. The sensor of claim 3, wherein the mechanical pulse is generated by a pneumatic or hydraulic impulse.

5. The sensor of claim 3, wherein the mechanical pulse is generated by an electromagnet or a magneto-strictive material and wherein the detection of the pulse is recorded by a detection coil or by a variable capacitor, light diode, accelerometer, microphone or any other sensitive pick up devices capable of monitoring the impact of the mechanical pulse.

6. The sensor of claim 5, wherein the mechanical pulse is a single pulse, a pulse train or in the form of vibration.

7. A sensor in accordance with claim 1, wherein a rate of the change of glucose values is computed and wherein the rate is shown on a display either in digits and/or graphs with associated warnings and recommendations to the user.

* * * * *